United States Patent [19]

Shiozaki et al.

[11] Patent Number: 4,851,414
[45] Date of Patent: Jul. 25, 1989

[54] ANTI-DEMENTIA AGENT

[75] Inventors: Shizuo Shiozaki, Fuji; Katsuichi Shuto, Mishima; Yoshimasa Oiji, Shizuoka, all of Japan

[73] Assignee: Kyowa Hakko Kagyo Co., Ltd., Tokyo, Japan

[21] Appl. No.: 229,824

[22] Filed: Aug. 8, 1988

[30] Foreign Application Priority Data

Aug. 10, 1987 [JP] Japan ................. 62-199518

[51] Int. Cl.$^4$ ........................... A61U 31/435
[52] U.S. Cl. ................................. 514/277
[58] Field of Search ........................ 514/277

[56] References Cited
FOREIGN PATENT DOCUMENTS 32629  3/1985  Japan .

OTHER PUBLICATIONS

Chem. Abst., (87)–53093K and 201329 J (1977).

Primary Examiner—Stanley J. Friedman
Attorney, Agent, or Firm—Fitzpatrick, Cella, Harper & Scinto

[57] ABSTRACT

Disclosed are anti-dementia agents comprising an antiamnestically effective amount of a benzylpyridine derivative of the formula

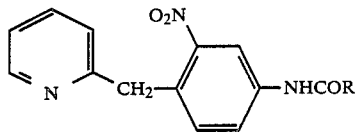

wherein R is an alkyl group. The invention also pertains to the treatment of dementia by administration of such anti-dementia agent.

4 Claims, No Drawings

ANTI-DEMENTIA AGENT

BACKGROUND OF THE INVENTION

The present invention relates to an anti-dementia agent, and more particularly to an anti-dementia agent comprising an antiamnestically effective amount of a benzylpyridine derivative.

It is disclosed in Japanese Published Examined Patent Application No. 32629/85 that benzylpyridine derivatives related to the present invention possess an antidepressive and antiinflammatory activity. However, it is unknown that these compounds have an antiamnestic activity and therefore, their use as an anti-dementia agent is unknown.

With the prolongation of the average span of life in recent years, the number of people with senile dementia has been rapidly increasing. Such people are afflicted with memory loss often accompanied with wandering, unclean and dangerous behavior or symptoms such as personality change and allophasis.

To treat senile dementia, a variety of drugs have been administered to patients in the clinical field.

Representative examples include cerebral metabolism activators such as idebenone, calcium hopatenate, and amantadine hydrochloride; cerebrovasodilators such as vinpocetine and dihydroergotoxin mesylate, (described in "Senile Dementia and Anti-dementia Agents—Aiming at Developing New Anti-dementia Agents", edited by Kenji Kosaka and Takeshi Ishii, Japan Society for Science and Technology (1987)); and oxiracetam, an experimental treatment.

Use of these drugs alleviates subjective symptoms relating to emotion. However, the main symptoms of senile dementia involving deterioration of intellectual functions such as decrease in impressibility and disorientation, are not necessarily alleviated by these treatments. Therefore, it is desirable to develop new drugs which alleviate symptoms of memory deterioration such as impressibility and orientation. To this end, it has been found that certain benzylpyridine derivatives have a strong antiamnestic activity and are thus useful as anti-dementia agents.

SUMMARY OF THE INVENTION

The present invention provides an anti-dementia agent comprising as an antiamnestically effective amount of a benzylpyridine derivative [hereinafter referred to as Compound (I)] represented by formula (I):

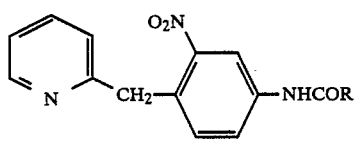

(I)

wherein R represents an alkyl group and pharmaceutically acceptable acid addition salts thereof.

In the definition of R in formula (I), the alkyl group represents a straight-chain or branched alkyl group having 1 to 17 carbon atoms, and includes methyl, ethyl, propyl, isopropyl, butyl, isobutyl, t-butyl, pentyl, hexyl, heptyl, octyl, nonyl, decyl, undecyl, dodecyl, tridecyl, tetradecyl, pentadecyl, hexadecyl and heptadecyl groups.

Specific examples of Compound (I) useful in the present invention include the following compounds.

1. α-(p-Acetylamino-o-nitrobenzyl)pyridine (Compound A)
2. α-(p-Butyrylamino-o-nitrobenzyl)pyridine (Compound B)
3. α-(p-Valerylamino-o-nitrobenzyl)pyridine (Compound C)
4. α-(p-Hexanoylamino-o-nitrobenzyl)pyridine (Compound D)
5. α-(p-Octanoylamino-o-nitrobenzyl)pyridine (Compound E)
6. α-(p-Decanoylamino-o-nitrobenzyl)pyridine (Compound F)
7. α-(p-Myristylamino-o-nitrobenzyl)pyridine (Compound G)
8. α-(p-Stearylamino-o-nitrobenzyl)pyridine (Compound H)

The properties of these compounds are summarized in Table 1.

TABLE 1

| Compound | R in General Formula (I) | Melting Point (°C.) | Molecular Formula |
|---|---|---|---|
| A | $CH_3$ | 159–160 | $C_{14}H_{13}N_3O_3$ |
| B | $(CH_2)_2CH_3$ | 124 | $C_{16}H_{17}N_3O_3$ |
| C | $(CH_2)_3CH_3$ | 96–97 | $C_{17}H_{19}N_3O_3$ |
| D | $(CH_2)_4CH_3$ | 70–73 | $C_{18}H_{21}N_3O_3$ |
| E | $(CH_2)_6CH_3$ | 92–93 | $C_{20}H_{25}N_3O_3$ |
| F | $(CH_2)_8CH_3$ | 69–70 | $C_{22}H_{29}N_3O_3$ |
| G | $(CH_2)_{12}CH_3$ | 83–84 | $C_{26}H_{37}N_3O_3$ |
| H | $(CH_2)_{16}CH_3$ | 87–88 | $C_{30}H_{45}N_3O_3$ |

The present invention further provides a method of treating dementia comprising daily administration of an antiamnestically effective amount of a benzylpydrine derivative.

DETAILED DESCRIPTION

Compounds A–H are known compounds described in Japanese Published Examined Patent Application No. 32629/85 or compounds which can be prepared by known methods.

For example, Compound (I) results form acylating α-(p-amino-o-nitrobenzyl)pyridine represented by formula (II):

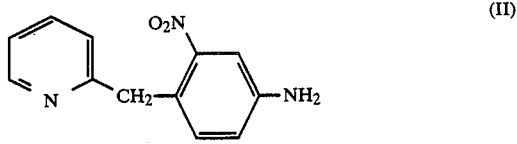

(II)

with an acylating agent represented by formula (III):

RCOOH  (III)

wherein R has the same significance as described above or an acylating agent functionally equivalent thereto (for example, acid anhydrides, acid halides, and activated esters) in a suitable solvent.

Compound C is not described in said publication, and a process for preparing Compound C is described in the Reference Example.

Compound (I) which is the active ingredient in the present invention can be used as a free base or in the form of pharmaceutically acceptable acid addition salts. Suitable examples of the salts are hydrochlorides, hydrobromides, sulfates, phosphates, acetates, oxalates, succinates, malates, tartrates, citrates, fumarates, etc. The salts are readily formed by treating Compound (I) with the corresponding acid in a conventional manner.

Although compound (I) or acid addition salts thereof may be used alone, they are typically formulated into various pharmaceutically acceptable preparations. Such a pharmaceutical composition can be prepared by uniformly mixing an antiamnestically effective amount of Compound (I) or an acid addition salt thereof as the active ingredient and a pharmaceutically acceptable carrier. The carrier can take various forms depending upon the form of preparation desired for administration. These pharmaceutical compositions are preferably in a unit dose form suited for oral administration or administration through injection.

For the preparation of compositions in a form suited for oral administration, any useful pharmaceutically-acceptable carriers can be used. For example, oral liquid preparations such as a suspension and a syrup can be prepared using water, sugars such as sucrose, sorbitol and fructose, glycols such as polyethylene glycol and propylene glycol, oils such as sesame oil, olive oil and soybean oil, aseptics such as alkyl p-hydroxybenzoates, flavors such as strawberry flavor and peppermint, etc.

Powders, pills, capsules and tablets can be prepared using excipients such as lactose, glucose, sucrose, mannitol and Avicel, disintegrators such as starch and sodium alginate, lubricants such as magnesium stearate and talc, binders such as polyvinyl alcohol, hydroxypropyl cellulose and gelatin, surface active agents such as fatty acid esters, plasticizers such as glycerine, etc.

Tablets and capsules are most useful unit oral preparations due to the readiness of administration. For the preparation of tablets and capsules, solid pharmaceutical carriers are used.

A solution injection can be prepared using a carrier such as distilled water, a salt solution, a glucose solution or a mixture of a salt solution and a glucose solution.

The effective dose and the administration schedule of Compound (I) or pharmaceutically acceptable acid addition salts thereof vary depending upon mode of administration, age, body weight and conditions of a patient, etc., but generally, it is desirable to give the effective compound in a daily dose of 5 to 500 mg, preferably 20 to 100 mg at one time or in 2 to 3 parts.

Compound (I) used in the present invention has an excellent antiamnestic activity. The following experiments tested the antiamnestic activity of Compound (I) and the toxicity thereof. The antiamnestic activity was measured by using the light-and-dark box method. Symbols of the test compounds correspond to said compounds (Table 1).

EXPERIMENT 1

Activity on Electroconvulsive Shock-induced Amnesia

As the test animals, 14 to 15 dd strain male mice (body weight: 23–28 g) were used for each group. As the experimental device, a step-through type passive avoidance training box composed of a light room and a dark room (light room: $130 \times 90 \times 90$ mm; dark room $180 \times 90 \times 90$ mm) was used.

In the acquisition trial where learning takes place, mice put in the light room move to the dark room. Each time the mice entered the dark room, electric stimulation of 0.25 mA was given to four limbs of each mouse for 2 seconds from grids on the floor.

Amnesia-inducing treatment was performed by electroconvulsive shock (2,000 V, 25 mA, 0.2 seconds) immediately after completion of the acquisition trial. After 24 hours, the test trial was conducted to measure the length of time before the mice entered the dark room. This time period, termed the reaction latent time, was recorded. A reaction latent time longer than 600 seconds was recorded as 600 seconds.

A test compound was suspended in 0.3% sodium carboxymethyl cellulose (hereinafter referred to as "CMC"). That suspension and a control of 0.3% CMC without any test compound were respectively administered to the mice 60 minutes prior to each test trial.

The effect was evaluated by Student-t test to determine whether there was a significant difference in reaction latent time between the amnesia control group and the group administered with the test compound in the passive avoidance test trial. The results are shown in Tables 2-1 to 2-6.

TABLE 2-1

| Test Compound | Dose (mg/kg, oral) | Amnesia-inducing Treatment | Number of Animals Used | Test Trial Mean Reaction Latent Time (second) | Comparison with Amnestic Control Group (t-test) |
|---|---|---|---|---|---|
| Normal control | — | — | 15 | 391.1 ± 42.6 | — |
| Amnestic control | — | + | 29 | 76.0 ± 14.3 | $P < 0.001$* |
| Compound B | 5 | + | 14 | 76.3 ± 10.6 | no significant difference |
| " | 10 | + | 14 | 146.7 ± 31.1 | $P < 0.05$ |
| " | 20 | + | 15 | 114.5 ± 28.0 | no significant difference |
| " | 40 | + | 15 | 135.2 ± 27.4 | $P < 0.05$ |
| " | 80 | + | 15 | 144.9 ± 32.3 | $P < 0.05$ |
| " | 160 | + | 15 | 204.9 ± 35.6 | $P < 0.001$ |
| Amnestic control | — | + | 30 | 60.2 ± 12.7 | — |
| Compound A | 20 | + | 15 | 90.5 ± 37.5 | no significant difference |
| " | 40 | + | 15 | 160.5 ± 49.6 | $P < 0.05$ |
| " | 80 | + | 15 | 253.7 ± 61.6 | $P < 0.001$ |
| Compound C | 80 | + | 15 | 172.8 ± 60.2 | $P < 0.01$ |
| Normal control | — | — | 15 | 330.5 ± 39.9 | — |
| Amnestic | — | + | 30 | 47.5 ± 7.5 | $P < 0.0001$* |

TABLE 2-1-continued

Antiamnestic Activity (mouse)

| Test Compound | Dose (mg/kg, oral) | Amnesia-inducing Treatment | Number of Animals Used | Test Trial Mean Reaction Latent Time (second) | Comparison with Amnestic Control Group (t-test) |
|---|---|---|---|---|---|
| control | | | | | |
| Compound D | 20 | + | 15 | 86.9 ± 12.5 | $P < 0.05$ |
| " | 40 | + | 15 | 203.1 ± 40.4 | $P < 0.0001$ |
| " | 80 | + | 15 | 274.8 ± 60.9 | $P < 0.0001$ |
| " | 160 | + | 15 | 243.4 ± 52.5 | $P < 0.0001$ |
| Normal control | — | — | 15 | 451.3 ± 41.5 | — |
| Amnestic control | — | + | 30 | 100.9 ± 8.5 | $P < 0.0001$* |
| Compound G | 20 | + | 15 | 138.9 ± 22.2 | no significant difference |
| " | 40 | + | 15 | 110.5 ± 25.4 | " |
| " | 80 | + | 15 | 136.3 ± 17.6 | " |
| " | 160 | + | 15 | 247.7 ± 58.0 | $P < 0.01$ |
| Normal control | — | — | 15 | 451.8 ± 32.8 | — |
| Amnestic control | — | + | 30 | 82.3 ± 11.8 | $P < 0.0001$* |
| Idebenone | 2.5$^a$ | + | 15 | 65.9 ± 10.8 | no significant difference |
| " | 5 | + | 15 | 124.3 ± 20.3 | " |
| " | 10 | + | 15 | 69.5 ± 18.9 | " |
| " | 20 | + | 15 | 73.3 ± 12.3 | " |
| Calcium Hopatenate | 160$^a$ | + | 12 | 187.4 ± 57.5 | $P < 0.05$ |
| " | 320 | + | 12 | 138.3 ± 32.8 | no significant difference |
| Vinpocetine | 2.5$^a$ | + | 15 | 90.2 ± 37.9 | " |
| " | 5 | + | 15 | 86.2 ± 18.6 | " |
| " | 10 | + | 15 | 72.3 ± 15.2 | " |
| Dihydro-ergotoxin mesylate | 1.25$^a$ | + | 15 | 99.5 ± 16.5 | " |
| " | 2.5 | + | 15 | 91.5 ± 17.3 | " |
| " | 5 | + | 15 | 71.3 ± 18.1 | " |
| Oxiracetam | 20$^b$ | + | 12 | 112.5 ± 40.0 | " |
| " | 40 | + | 12 | 205.9 ± 54.2 | $P < 0.05$ |
| " | 80 | + | 12 | 151.3 ± 44.0 | no significant difference |
| Normal control | — | — | 15 | 433.0 ± 47.4 | — |
| Amnestic control | — | + | 26 | 172.2 ± 30.4 | $P < 0.0001$* |
| Amitriptyline | 10 | + | 15 | 147.3 ± 37.6 | no significant difference |
| " | 20 | + | 12 | 198.6 ± 51.5 | " |
| " | 40 | + | 14 | 134.9 ± 28.1 | " |
| " | 80 | + | 9 | 84.1 ± 17.9 | " |
| Desipramine | 10 | + | 13 | 163.2 ± 51.7 | " |
| " | 20 | + | 15 | 111.2 ± 26.1 | " |
| " | 40 | + | 14 | 115.4 ± 38.8 | " |
| " | 80 | + | 14 | 80.4 ± 16.1 | $P < 0.05$ |
| Imipramine | 10 | + | 15 | 236.3 ± 52.6 | no significant difference |
| " | 20 | + | 14 | 263.4 ± 59.1 | " |
| " | 40 | + | 15 | 180.0 ± 47.9 | " |
| " | 80 | + | 14 | 174.9 ± 44.5 | " |

*Comparison with Normal Control Group (the same shall apply hereinafter.)
$^a$intraperitoneal administration
$^b$oral administration As is evident from the experimental results shown above, the reaction latent time was significantly ($P<0.0001$) shortened by the amnesia-inducing treatment (electro-convulsive shock) in the amnestic control group, compared with the normal control group. With Compound B in Table 2-1, the reaction latent time was significantly prolonged at doses of 10, 40, 80 and 160 mg/kg, compared with the amnestic control group. Also with Compounds A, C, D and G in Tables 2-2, 2-3 and 2-4, the reaction latent time was prolonged.

Table 2-5 shows the results with various control drugs. None of them resulted in a significant improvements in performance over the amnestic control group.

Table 2-6 shows the results with antidepressants as reference compounds. The three drugs all caused remarkable change in behavior. In particular, ataxis in motor coordination is remarkable. The order of its intensity was:

amitriptyline > desipramine > imipramine

In general, a worsening tendency was noted in high doses (40 to 80 mg/kg). Although some results showed a tendency of prolonging the reaction latent time (10 and 20 mg/kg), there was no significant difference and thus the results are not considered as an evidence for specific effect.

EXPERIMENT 2

Activity on Scopolamine-induced Amnesia

As the test animals, 10 to 30 Wistar strain male rats (body weight: 250–300 g) were used for each group. As the experimental device, a step-through type passive avoidance training box composed of a light room and a dark room (light room: 400×400×400 mm; dark room 200×150×200 mm) was used.

In the acquisition trial where learning is made, rats put in the light room move to the dark room. Each time the rats entered the dark room, electric stimulation of 2 mA was given to four limbs of each rat for 3 seconds from grids on the floor.

Amnesia-inducing treatment was performed by intraperitoneal administration of scopolamine in a dose of 1.5 mg/kg 30 minutes prior to the acquisition trial (training). The test trial was carried out 24 hours after the training and the reaction latent time was measured in a similar manner as in Experiment 1.

Test Compound B and idebenone were suspended in 0.3% CMC, and imipramine was dissolved in physiological saline. Compound B and imipramine were orally administered 60 minutes before the training and idebenone was intraperitoneally administered 30 minutes before the training. The results are shown in Table 3.

EXPERIMENT 3

Activity on Amnesia due to Damage of Basal Forebrain

As the test animals, 13 to 39 Wistar strain male rats (body weight: 250–300 g) were used for each group. Amnesia-inducing treatment was effected by damaging the basal forebrain through injection of 0.2 $\mu g/\mu l$ kainic acid at the basal forebrain from both sides under anesthesia with pentobarbital-Na.

After the recovery period of about 10 days following the operation, the trial for acquiring learning (training) was performed in a similar manner using the same experimental device as in Experiment 2. After 24 hours, the test trial was carried out.

Measurement of the latent time was carried out in a similar manner as in Experiment 1. Test Compound B and idebenone were suspended in 0.3% CMC, and the suspension was administered twice 60 minutes prior to the training and 60 minutes prior to the test.

Alternatively, the suspension was administered for 9 consecutive days after the recovery period. In this case, Compound B was orally administered and idebenone was intraperiotoneally administered; and the training was conducted on day 8 and the test trial was conducted on day 9.

The test method using the rats with basal forebrain lesion shows an antiamnestic activity on a model of Alzheimer disease. Namely, in a human patient with senile dementia of the Alzheimer type showing memory deficits as a main symptom, choline acetyltransferase activity in the cerebral cortex and hippocampus is markedly reduce.d This is due to remarkable fall off of

TABLE 3

| | | | Antiamnestic Activity (rat) | | |
|---|---|---|---|---|---|
| Test Compound | Dose (mg/kg) | Amnesia-inducing Treatment | Number of Rats that Reached Standard Point[a] Number of Rats Tested | Test Trial Mean Reaction Latent Time (second) | Comparison with Amnestic Control Group (t-test) |
| Normal control | — | — | 14/21 | 466.1 ± 45.3 | — |
| Amnestic control | — | + | 0/30 | 54.7 ± 9.9 | $P < 0.0001$* |
| Compound B | 2.5 | + | 1/20 | 94.3 ± 30.3 | No significant difference |
| " | 5 | + | 3/17 | 148.9 ± 54.3 | $P < 0.05$ |
| " | 10 | + | 4/20 | 201.2 ± 55.5 | $P < 0.01$ |
| " | 20 | + | 2/17 | 172.4 ± 52.6 | $P < 0.01$ |
| " | 40 | + | 4/20 | 171.2 ± 52.5 | $P < 0.05$ |
| Amnestic control | — | + | 0/10 | 95.2 ± 44.8 | $P < 0.001$ |
| Idebenone | 2.5 | + | 0/10 | 58.4 ± 19.7 | no significant difference |
| " | 5 | + | 0/10 | 110.6 ± 30.2 | " |
| " | 10 | + | 0/10 | 148.8 ± 60.2 | " |
| Amnestic control | — | + | 1/26 | 128.1 ± 28.2 | $P < 0.001$ |
| Imipramine | 20 | + | 1/13 | 110.4 ± 44.3 | no significant difference |
| " | 40 | + | 1/13 | 186.6 ± 54.0 | " |

[a]Standard point: 600 seconds

As is seen from the results in Table 3, Compound B showed an antiamnestic activity by oral administration in a dose of 5 to 40 mg/kg, but idebenone and imipramine showed no antiamnestic activity.

nerve cells in nucleus basalis Meynert, which is the initiating nucleus of cholinergic neuron, responsible for projection on the cerebral cortex. Lesion of the basal forebrain corresponding to nucleus basalis Meynert in rats causes disturbance in learning. The results in the learning-disturbed model animals are shown in Table 4.

TABLE 4

Antiamnestic Activity (rat)

| Test Compound | Dose (mg/kg) | Amnesia-inducing Treatment | Number of Rats that Reached Standard Point[a] Number of Rats Tested | Test Trial Mean Reaction Latent Time (second) | Comparison with Amnestic Control Group (t-test) |
|---|---|---|---|---|---|
| Normal control | — | — | 8/13 | 442.2 ± 69.2 | — |
| Sham-lesion control | — | — | 6/13 | 364.7 ± 70.3 | no significant difference[d] |
| Lesion control | — | + | 0/39 | 45.0 ± 15.3 | $P < 0.001$[e] |
| Compound B[b] | 2.5 | + | 1/19 | 121.8 ± 36.5 | $P < 0.05$[f] |
| " | 5 | + | 5/19 | 215.5 ± 60.0 | $P < 0.001$ |
| " | 10 | + | 3/18 | 191.2 ± 57.7 | $P < 0.01$ |
| " | 20 | + | 4/18 | 209.2 ± 60.2 | $P < 0.001$ |
| " | 40 | + | 2/18 | 163.0 ± 51.5 | $P < 0.01$ |
| Idebenone[b] | 10 | + | 0/14 | 52.0 ± 22.1 | no significant difference[f] |
| " | 20 | + | 0/14 | 15.2 ± 3.4 | " |
| " | 40 | + | 0/14 | 27.7 ± 8.9 | " |
| Lesion control | — | + | 2/24 | 104.0 ± 35.2 | $P < 0.001$[e] |
| Compound B[c] | 2.5 | + | 4/13 | 243.2 ± 73.7 | no significant difference[f] |
| " | 10 | + | 5/13 | 259.0 ± 78.5 | $P < 0.05$ |
| Idebenone[c] | 2.5 | + | 7/13 | 382.8 ± 80.2 | $P < 0.01$[f] |
| " | 10 | + | 3/13 | 178.2 ± 68.2 | no significant difference. |

[a]Standard point: 600 seconds
[b]Administered twice
[c]Administered for 9 days
[d]Compared with the normal control group
[e]Compared with the sham-lesion control group
[f]Compared with the lesion control group As shown in Table 4, Compound B showed an activity of alleviating learning disturbance when administered twice in a dose of 2.5 mg/kg or more. Idebenone showed no improving effect when administered twice in a similar manner in a dose of 10 to 40 mg/kg. On the other hand, in administration for 9 consecutive days, a significant ($P<0.05$) improving activity was noted with Compound B in a dose of 10 mg/kg. With idebenone, an apparent improving effect was noted by intraperitoneal administration of 2.5 mg/kg. Thus, the effect was noted with Compound B both in administration of two equal doses and consecutive administration, whereas it was noted that idebenone showed the effect only in consecutive administration.

From the foregoing results, it is clear that Compound B shows an apparent improving activity in the learning-disturbed animal model.

EXPERIMENT 4

Acute Toxicity

Acute toxicity test was carried out by orally administering Compound (I) used in the present invention to mice (male) and rats (male). The results are shown in Table 5.

TABLE 5

| | Acute Toxicity (LD$_{50}$ mg/kg, oral) | |
|---|---|---|
| Test Compound | Mouse | Rat |
| A | 660 | >200 |
| B | 1534 | >850 |
| C | >300 | — |
| D | >1000 | >100 |
| E | >1000 | >100 |
| F | >1000 | >100 |

TABLE 5-continued

| | Acute Toxicity (LD$_{50}$ mg/kg, oral) | |
|---|---|---|
| Test Compound | Mouse | Rat |
| G | >1000 | >100 |

As shown in Table 5, all the compounds have only a weak toxicity and thus can be safely used over a wide range of dosages.

The results of the foregoing experiments show that the invention described herein is useful for treating individuals suffering from senile dementia, and the invention further describes the antiamnestically effective daily dosage and methods of dosage administration.

Certain embodiments of the invention are illustrated in the following examples.

EXAMPLE 1

Tablets 2000 tablets are prepared in a conventional manner, each having the following composition and containing 20 mg of the active ingredient.

Compound B (100 g), 600 g of lactose and 250 g of potato starch were mixed, and 400 g of 10% aqueous solution of hydroxypropyl cellulose was added to the mixture. The mixture was kneaded, granulated and dried in a conventional manner. Then the granules were made uniform to form granules for tabletting. After 10 g of the magnesium stearate was added, the mixture was formed into tablets using a tabletting machine (Kikusui, Model RT-15) equipped with a pestle having a diameter of 8 mm to give a preparation containing 20 mg of the active ingredient in one tablet.

| Formulation | |
|---|---|
| Compound B | 20 mg |
| Lactose | 120 mg |
| Patato starch | 50 mg |
| Hydroxypropyl cellulose | 8 mg |
| Magnesium stearate | 2 mg |
| | 200 mg |

EXAMPLE 2

Granules

Compound B (20 g), 640 g of lactose and 300 g of corn starch were mixed, and 400 g of 10% aqueous solution of hydroxypropyl cellulose was added to the mixture. The mixture was kneaded, granulated and dried in a conventional manner to give granules. In 1000 mg of the granules, 20 mg of the active ingredient was contained.

| Formulation | |
|---|---|
| Compound B | 20 mg |
| Lactose | 640 mg |
| Corn starch | 300 mg |
| Hydroxypropyl cellulose | 40 mg |
| | 1000 mg |

EXAMPLE 3

Capsules

Compound B (200 g), 995 g of Avicel and 5 g of magnesium stearate were mixed in a conventional manner. The mixture was loaded into hard capsule No. 4 with a capsule filling machine (Zanasi, Model LZ-64) (120 mg per capsule) to give capsules.

| Formulation | |
|---|---|
| Compound B | 20 mg |
| Avicel | 99.5 mg |
| Magnesium stearate | 0.5 mg |
| | 120 mg |

REFERENCE EXAMPLE

Preparation of α-(p-Valerylamino-o-nitrobenzyl)pyridine (Compound C)

To a solution of 2.5 g (10.9 mmol) of α-(p-amino-o-nitrobenzyl)pyridine in 25 ml of n-valeric acid was added 2.2 ml (11.2 mmol) of n-valeric anhydride. The mixture was heated at 90 to 100° C. for 4 hours. After the reaction mixture was allowed to cool to room temperature, the solvent was distilled off under reduced pressure, and 30 ml of water was added to the residue. Aqueous sodium hydroxide solution (10 N) was added dropwise with stirring and the crystals formed were taken by suction filtration. The crude crystals were recrystallized from methanol to give 1.86 g (59.8%) of Compound C as yellowish orange needles.

Melting point: 96°–97° C.

Elemental analysis (as $C_{17}H_{19}N_3O_3$).

Calc'd (%) C: 65.14 H: 6.11 N: 13.41. Found (%) C: 65.14 H: 6.15 N: 13.25. $^1H$ - NMR $\delta(CDCL_3)$: 0.92 (3H, t, J=2.4Hz), 1.39 (2H, m), 1.68 (2H, m), 2.34 (2H, t, J=2.4Hz), 4.44 (2H, s), 7.13–7.19 (2H, m), 7.22–7.31 (1H, m), 7.60–7.71 (2H, m), 8.05–8.09 (2H, m), 8.47–8.50 (1H, m).

What is claimed is:

1. A method of treating dementia which comprises administering to a patient suffering from dementia an antiamnestically effective amount of a benzylpyridine derivative of the formula:

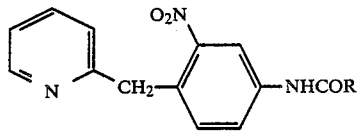

wherein R represents an alkyl group or a pharmaceutically acceptable acid addition salt thereof.

2. A method of treating dementia according to claim 1 wherein said pharmaceutically acceptable acid addition saltis are selected from the group consisting of hydrochloride, hydrobromide, sulfate, phosphate, acetate, oxalate, succinate, malate, tartrate, citrate and fumarate.

3. A method of treating dementia according to claim 1 wherein said antiamnestically effective amount comprises a daily dosage of from 5 to 500 mg.

4. A method of treating dementia according to claim 1 wherein said antiamnestically effective amount comprises a daily dosage of from 20 to 100 mg.

* * * * *

UNITED STATES PATENT AND TRADEMARK OFFICE
CERTIFICATE OF CORRECTION

PATENT NO. : 4,851,414

DATED : July 25, 1989

INVENTOR(S) : SHIZUO SHIOZAKI, ET AL.

It is certified that error appears in the above-identified patent and that said Letters Patent is hereby corrected as shown below:

COLUMNS 3-6:

The Tables bridging Columns 3-6 should read:

--Table 2-1. Antiamnestic Activity (mouse)

| Test Compound | Dose (mg/kg, oral) | Amnesia-inducing Treatment | Number of Animals used | Test Trial Mean Reaction Latent Time (second) | Comparison With Amnestic Control Group (t-test) |
|---|---|---|---|---|---|
| Normal Control | - | - | 15 | 391.1±42.6 | - |
| Amnestic Control | - | + | 29 | 76.0±14.3 | $P<0.001$* |
| Compound B | 5 | + | 14 | 76.3±10.6 | no significant difference |
| " | 10 | + | 15 | 146.7±3.1 | $P<0.05$ |
| " | 20 | + | 15 | 114.5±28.0 | no significant difference |
| " | 40 | + | 15 | 135.2±27.4 | $P<0.05$ |
| " | 80 | + | 15 | 144.9±32.3 | $P<0.05$ |
| " | 160 | + | 15 | 204.9±35.6 | $P<0.001$ |

* Comparison with Normal Control Group (the same shall apply hereinafter.)

UNITED STATES PATENT AND TRADEMARK OFFICE
CERTIFICATE OF CORRECTION

PATENT NO. : 4,851,414
DATED : July 25, 1989
INVENTOR(S) : SHIZUO SHIOZAKI, ET AL.

It is certified that error appears in the above-identified patent and that said Letters Patent is hereby corrected as shown below:

Table 2-2. Antiamnestic Activity (mouse)

| Test Compound | Dose (mg/kg, oral) | Amnesia-inducing Treatment | Number of Animals used | Test Trial Mean Reaction Latent Time (second) | Comparison With Amnestic Control Group (t-test) |
|---|---|---|---|---|---|
| Amnestic control | - | + | 30 | 60.±12.7 | - |
| Compound A | 20 | + | 15 | 90.5±37.5 | no significant difference |
| " | 40 | + | 15 | 160.5±49.6 | $P<0.05$ |
| " | 80 | + | 15 | 253.7±61.6 | $P<0.001$ |
| Compound C | 80 | + | 15 | 172.8±60.2 | $P<0.01$ |

Table 2-3. Antiamnestic Activity (mouse)

| Test Compound | Dose (mg/kg, oral) | Amnesia-inducing Treatment | Number of Animals used | Test Trial Mean Reaction Latent Time (second) | Comparison With Amnestic Control Group (t-test) |
|---|---|---|---|---|---|
| Normal control | - | - | 15 | 330.5±39.9 | - |
| Amnestic control | - | + | 30 | 47.5±7.5 | $P<0.0001$* |
| Compound D | 20 | + | 15 | 86.9±12.5 | $P<0.05$ |
| " | 40 | + | 15 | 203.1±40.4 | $P<0.0001$ |
| " | 80 | + | 15 | 274.8±60.9 | $P<0.0001$ |
| " | 160 | + | 15 | 243.4±52.5 | $P<0.0001$ |

UNITED STATES PATENT AND TRADEMARK OFFICE
CERTIFICATE OF CORRECTION

PATENT NO. : 4,851,414

DATED : July 25, 1989

INVENTOR(S) : SHIZUO SHIOZAKI, ET AL.

It is certified that error appears in the above-identified patent and that said Letters Patent is hereby corrected as shown below:

Table 2-4. Antiamnestic Activity (mouse)

| Test Compound | Dose (mg/kg, oral) | Amnesia-inducing Treatment | Number of Animals used | Test Trial Mean Reaction Latent Time (second) | Comparison With Amnestic Control Group (t-test) |
|---|---|---|---|---|---|
| Normal control | - | - | 15 | 451.3±41.5 | - |
| Amnestic control | - | + | 30 | 100.9±8.5 | $P<0.0001^*$ |
| Compound G | 20 | + | 15 | 138.9±22.2 | no significant difference |
| " | 40 | + | 15 | 110.5±25.4 | no significant difference |
| " | 80 | + | 15 | 136.3±17.6 | " |
| " | 160 | + | 15 | 247.7±58.0 | $P<0.01$ |

Table 2-5. Antiamnestic Activity of Control Drug (mouse)

| Test Compound | Dose (mg/kg, oral) | Amnesia-inducing Treatment | Number of Animals used | Test Trial Mean Reaction Latent Time (second) | Comparison With Amnestic Control Group (t-test) |
|---|---|---|---|---|---|
| Normal control | - | - | 15 | 451.8±32.8 | - |
| Amnestic control | - | + | 30 | 82.3±11.8 | $P<0.0001^*$ |

UNITED STATES PATENT AND TRADEMARK OFFICE
CERTIFICATE OF CORRECTION

PATENT NO. : 4,851,414
DATED : July 25, 1989
INVENTOR(S) : SHIZUO SHIOZAKI, ET AL.

It is certified that error appears in the above-identified patent and that said Letters Patent is hereby corrected as shown below:

| | | | | | |
|---|---|---|---|---|---|
| Idebedone | 2.5[a)] | + | 15 | 65.9±10.8 | no significant difference |
| " | 5 | + | 15 | 124.3±20.3 | " |
| " | 10 | + | 15 | 69.5±18.9 | " |
| " | 20 | + | 15 | 73.3±12.3 | " |
| Calcium Hopatenate | 160[a)] | + | 12 | 187.4±57.5 | $P<0.05$ |
| " | 320 | + | 12 | 138.3±32.8 | no significant difference |
| Vinpocetine | 2.5[a)] | + | 15 | 90.2±37.9 | " |
| " | 5 | + | 15 | 86.2±18.6 | " |
| " | 10 | + | 15 | 72.3±15.2 | " |
| Dihydro-ergotoxin mesylate | 1.25[a)] | + | 15 | 99.5±16.5 | " |
| " | 2.5 | + | 15 | 91.5±17.3 | " |
| " | 5 | + | 15 | 71.3±18.1 | " |
| Oxiracetam | 20[b)] | + | 12 | 112.5±40.00 | " |
| " | 40 | + | 12 | 205.9±54.2 | $P<0.05$ |
| " | 80 | + | 12 | 151.3±44.00 | no significant difference | a) intraperitoneal administration
b) oral administration

UNITED STATES PATENT AND TRADEMARK OFFICE
CERTIFICATE OF CORRECTION

PATENT NO. : 4,851,414
DATED : July 25, 1989
INVENTOR(S) : SHIZUO SHIOZAKI, ET AL.

It is certified that error appears in the above-identified patent and that said Letters Patent is hereby corrected as shown below:

Table 2-6. Antiamnestic Activity of Antidepressant (mouse)

| Test Compound | Dose (mg/kg, oral) | Amnesia-inducing Treatment | Number of Animals used | Test Trial Mean Reaction Latent Time (second) | Comparison With Amnestic Control Group (t-test) |
|---|---|---|---|---|---|
| Normal control | - | - | 15 | 433.0±47.4 | - |
| Amnestic control | - | + | 26 | 172.2±30.4 | P<0.0001* |
| Amitriptyline | 10 | + | 15 | 147.3±37.6 | no significant difference |
| " | 20 | + | 12 | 198.6±51.5 | " |
| " | 40 | + | 14 | 134.9±28.1 | " |
| " | 80 | + | 9 | 84.1±17.9 | " |
| Desipramine | 10 | + | 13 | 163.2±51.7 | " |
| " | 20 | + | 15 | 111.2±26.1 | " |
| " | 40 | + | 14 | 115.4±38.8 | " |
| " | 80 | + | 14 | 80.4±16.1 | P<0.05 |
| Imipramine | 10 | + | 15 | 236.3±52.6 | no significant difference |
| " | 20 | + | 14 | 263.4±59.1 | " |
| " | 40 | + | 15 | 180.±47.9 | " |
| " | 80 | + | 14 | 174.9±44.5 | " -- |

UNITED STATES PATENT AND TRADEMARK OFFICE
CERTIFICATE OF CORRECTION

PATENT NO. : 4,851,414

DATED : July 25, 1989

INVENTOR(S) : SHIZUO SHIOZAKI, ET AL.

It is certified that error appears in the above-identified patent and that said Letters Patent is hereby corrected as shown below:

COLUMN 6:

Line 62, "ments" should read --ment--;
Line 65, "ataxis" should read --ataxia--.

COLUMN 8:

Line 23, "intraperiotoneally" should read --intraperitoneally--;
Line 32, "reduce.d" should read --reduced.--.

COLUMN 10:

Line 64, "the" (first occurrence) should be deleted.

COLUMN 12:

Line 43, "saltis are" should read --salt is--.

Signed and Sealed this

Twelfth Day of November, 1991

Attest:

HARRY F. MANBECK, JR.

*Attesting Officer*  *Commissioner of Patents and Trademarks*